US00PP08949P

United States Patent [19]

Elliott

[11] Patent Number: Plant 8,949

[45] Date of Patent: Oct. 18, 1994

[54] NECTARINE TREE — ELLIOTT CULTIVAR

[75] Inventor: Bill K. Elliott, Silver City, N. Mex.

[73] Assignee: Stark Brothers Nurseries and Orchards Company, Louisiana, Mo.

[21] Appl. No.: 154,460

[22] Filed: Nov. 19, 1993

[51] Int. Cl.[5] ..... A01H 5/00
[52] U.S. Cl. ..... Plt./41.3
[58] Field of Search ..... Plt. 41.3, 40.1, 41.1

*Primary Examiner*—James R. Feyrer
*Attorney, Agent, or Firm*—Burns, Doane, Swecker & Mathis

[57] ABSTRACT

The new nectarine cultivar originated as a limb mutation of unknown causation on a tree present in a young orchard of the N.J. 260 peach cultivar (U.S. Plant Pat. No. 4,572). The new cultivar is substantially similar to the N.J. 260 cultivar with the exception that the fruit is that of a nectarine and lacks pubescence. The fruit of the new cultivar commonly ripens a few days earlier than the late-ripening N.J. 260 cultivar, and its fruit commonly is slightly smaller than that of the N.J. 260 cultivar. The new cultivar generally can be grown in the northern fruit production areas of the United States where the N.J. 260 cultivar is grown.

2 Drawing Sheets

SUMMARY OF THE INVENTION

The new cultivar of nectarine tree (i.e., *Prunus*×*domestica* Risso) was discovered as a limb mutation of unknown causation on a peach tree growing in a young orchard of the N.J. 260 cultivar (U.S. Plant Pat. No. 4,572) near Fairfield, Ill. The orchard of such N.J. 260 trees had been planted during the mid-1980's. I was attracted to new cultivar primarily because of the absence of pubescence on the surface of its fruit. Unlike that of its parent, the fruit uniformly possessed a smooth and glossy finish characteristic of a nectarine. Had I not discovered and preserved the new cultivar it would have been lost to mankind.

The parent N.J. 260 cultivar originated during a breeding program carried out by Catherine H. Bailey and L. Frederic Hough at Rutgers, The State University of New Jersey, New Brunswick, N.J. Such parent variety was selected during 1972 from a population of seedlings resulting from the controlled cross pollination of an unnamed New Jersey seedling No. 585414 with pollen from the AUTUMNGLO cultivar (non-patented in the United States). The N.J. 260 cultivar is marketed under the STARK and ENCORE trademarks by Stark Brothers Nurseries and Orchards Company of Louisiana, Mo. It presently is a widely grown late-maturing peach cultivar for the Mid-Atlantic, North-Eastern, and North-Central regions of the United States. It is popular in most northern peach production areas due to its fruit quality, freestone pit, large fruit size, resistance to bacterial leaf spot caused by *Xanthomonas pruni*, and a high degree of cold-hardiness and return bloom. The N.J. 260 peaches commonly mature in early to late September which is relatively late in the peach commercial harvest season.

Following detailed observation it was concluded that a significant mutation had taken place on a southwest oriented single limb of a single peach tree of the N.J. 260 cultivar. The fruit formed on such limb possessed a distinctive glabrous finish characteristic of a nectarine. Also, the same or similar superior characteristics of N.J. 260 cultivar in other areas were well retained.

It was found that the new late-maturing nectarine cultivar of the present invention possesses the following combination of characteristics:

(a) forms fruit of good flavor and texture that is substantially similar to that of the N.J. 260 cultivar with the exception that it is lacking in pubescence,
(b) forms fruit that commonly matures approximately 3 to 5 days earlier than that of the N.J. 260 cultivar,
(c) forms fruit that commonly is slightly smaller than that of the N.J. 260 cultivar, and
(d) exhibits an overall growth habit that is substantially similar to that of the N.J. 260 cultivar.

The color pattern on the fruit of the new nectarine cultivar tends to be more mottled. When under-ripe or shipping-ripe the fruit flesh texture of the new variety tends to be slightly more dense and slightly more rubbery. The pit of the new cultivar commonly is slightly larger on average. The axial diameter of the fruit of the new cultivar tends to be slightly smaller in proportion to the transverse diameter thereby giving the fruit of the new cultivar a more globose configuration than the occasionally ovoid-shaped peach of the N.J. 260 cultivar.

The new variety has been asexually reproduced by topworking. For instance, limbs of the new cultivar were topworked during March, 1991 into the tops of trees of the N.J. 260 and JUNE PRINCE (non-patented in the United States) cultivars that were planted during 1986 and 1987 near Kelso, Mo. The characteristics of the new cultivar have been found to be stable and to be capable of transmission through succeeding generations by these and other asexual propagations.

The new cultivar has been named the ELLIOTT cultivar, and is being marketed under the ENCORE trademark by Stark Brothers Nurseries and Orchards Company of Louisiana, Mo.

BRIEF DESCRIPTION OF THE PHOTOGRAPHS

The accompanying photographs show typical specimens of the ELLIOTT new nectarine cultivar as depicted in color as nearly true as it is reasonably possible to make the same in color illustrations of this character. The specimens were obtained from the original limb mutation of the new cultivar being grown near Fairfield, Ill.

FIG. 1 illustrates various views of the fruit and a typical branch with leaves harvested at maturity on Aug. 30, 1992. The photograph was taken on Aug. 31, 1992. The views of the fruit illustrate the pistillate end, the stem end, the side with the most color, the side with the least color of a well-colored fruit, and sections in the transverse plane and in the suture plane with the entire pit intact.

FIG. 2 illustrates on the right typical whole fruits and fruit sections of the new nectarine cultivar. On the left are shown for comparative purposes similar views of the fruit of the N.J. 260 peach cultivar. The fruit specimens depicted illustrate pistillate ends, stem ends, side views, and axial sections in the suture plane with and without the pit. The photograph was prepared during early September 1991.

FIG. 3 illustrates on the right fruits of the new nectarine cultivar. On the left are shown fruits of the N.J. 260 peach cultivar. For each cultivar, fruit specimens are depicted that illustrate the pistillate end, the stem end, a side view with the most color, a side view with the least color of a well-colored fruit, and axial sections with and without the pit. The specimens were harvested on Aug. 30, 1992.

DETAILED DESCRIPTION

Figure 1:
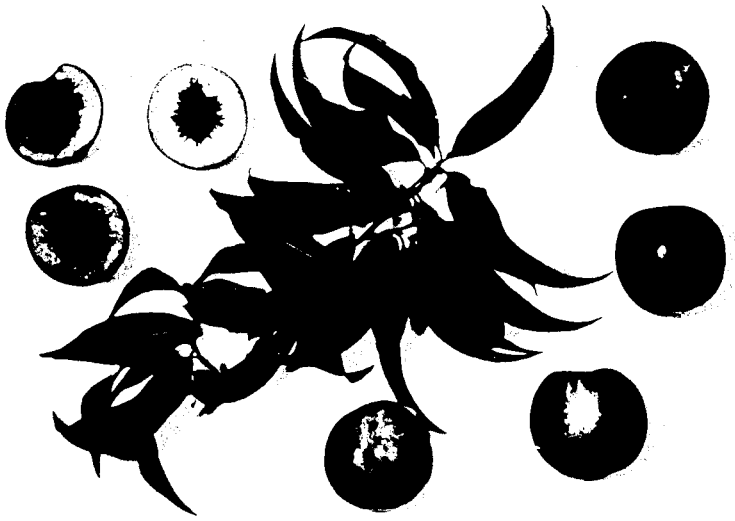
Figure 2:
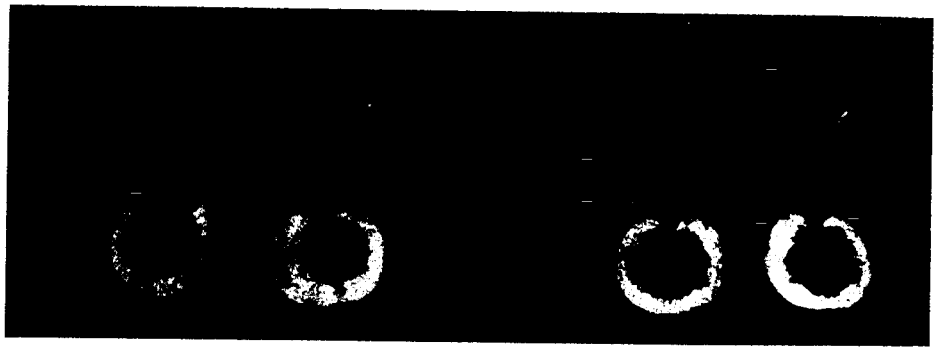
Figure 3:
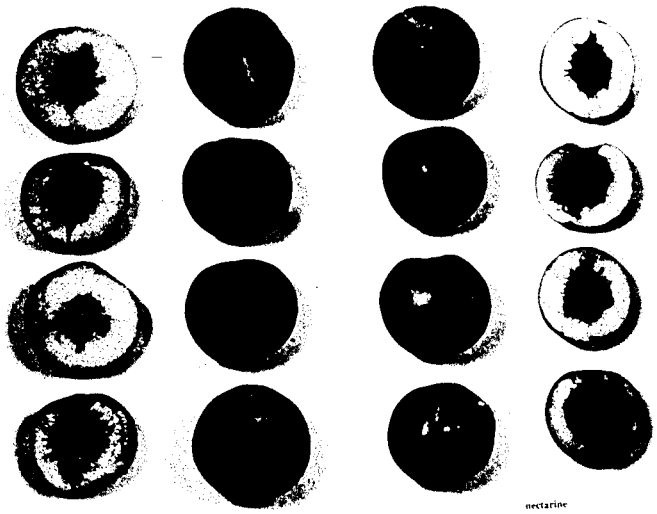

Reference is made in the following description to The R.H.S. Colour Chart of The Royal Horticultural Society, London, England.

Tree: Large size, vigorous, spreading growth habit, hardy, and substantially similar in overall appearance to N.J. 260 cultivar (U.S. Plant Pat. No. 4,572).

*Trunk.*—Medium thick, and moderately textured.

*Branches.*—Medium thick, and moderately textured with an average branching frequency.

*Bark.*—Substantially similar to the N.J. 260 peach cultivar. On the current year's growth, the bark at the distal one-third is Yellow-Green Group 144B; Red-Purple Group 59A to 59B coloration commonly appears on sun-exposed surfaces; anthocyanin pigmentation becomes more pronounced in the fall; basal portions have rugose vertically oriented slightly raised bark netting of Grey-Brown Group 199B to 199C randomly dotted with horizontally oriented ovoid-shaped raised lenticels of Greyed-Orange Group 164C; both the bark netting and the raised lenticels decrease in occurrence distally; the distal one-third commonly is substantially lacking in netting and raised lenticels; and the basal one-third commonly is nearly completely covered with netting and lenticels. On the previous year's growth, the bark is almost completely covered with rugose netting of Grey-Brown Group 199A; and there are numerous raised medium-sized elliptical lenticels of Greyed-Orange Group 164A with occasional patches of glabrous green bark. On the two year-old growth, the bark is smooth and not shiny; is lacking in the netting pattern; is Greyed-Green Group 197A to 197B in coloration; and possesses numerous raised medium-sized elliptical lenticels of Greyed-Orange Group 164A.

*Buds.*—Small to medium in size; narrow; acute; commonly possess moderately glabrous bud scales at the base and are slightly to moderately pubescent near the apex.

*Shape.*—Varies from elongated-ovate to elongated-obovate.

*Apex.*—Varies from acute to acuminate.

*Size.*—Tables 1 and 2 provide a comparison of vigorous terminal leaf dimensions of the new ELLIOTT nectarine cultivar and the N.J. 260 peach cultivar. The similarity in the dimensions of the leaves is apparent. In TABLE 1, 15 leaves of each cultivar were obtained during 1992 from trees being grown near Fairfield, Ill., and included leaves obtained from the original limb mutation of the new nectarine cultivar. In TABLE 2, 36 leaves of each cultivar were obtained during 1993 from trees being grown at a Kelso, Mo. test orchard. During such leaf evaluation the new nectarine cultivar had been topworked into trees of the N.J. 260 cultivar.

TABLE 1

| | N.J. 260 Peach | | | ELLIOTT Nectarine | | |
|---|---|---|---|---|---|---|
| | Minimum | Maximum | Average | Minimum | Maximum | Average |
| Width (W) | 2.54 cm. | 3.30 cm. | 3.00 cm. | 2.67 cm. | 3.30 cm. | 2.90 cm. |
| Length (L) | 9.02 cm. | 11.81 cm. | 10.70 cm. | 8.13 cm. | 12.32 cm. | 10.90 cm. |
| W:L Ratio | — | — | 0.28 | — | — | 0.27 |

TABLE 2

| | N.J. 260 Peach | | | ELLIOTT Nectarine | | |
|---|---|---|---|---|---|---|
| | Minimum | Maximum | Average | Minimum | Maximum | Average |
| Width (W) | 2.5 cm. | 4.1 cm. | 3.2 cm. | 2.4 cm. | 3.6 cm. | 3.0 cm. |
| Length (L) | 10.9 cm. | 17.4 cm. | 15.0 cm. | 11.9 cm. | 15.3 cm. | 13.7 cm. |
| W:L Ratio | — | — | 0.21 | — | — | 0.22 |

*Color.*—Medium green, the dorsal leaf surface of mature leaves during late summer and fall is Yellow-Green Group 146A, the ventral leaf surface of mature leaves during late summer and fall is Yellow-Green Group 146B, and the leaf coloration is not noticeably lighter or darker than that of the N.J. 260 peach cultivar.

*Surface texture.*—Both dorsal and ventral surfaces are glabrous, and the dorsal surface tends to be shinier than that of the ventral surface.

*Glands.*—Medium large in size, slightly reinform, slightly appressed, varying from opposite to alternate, and averaging three in number.

*Leaf margin.*—Finely and simply serrate, occasionally crenate, occasionally the margins on a single leaf may alternate between simply serrate and compoundly serrate, and when exposed to the sun during late summer and early fall commonly are edged with Red-Purple Group 59A and are slightly glandular at the base with 0 to 3 glands (most commonly 1, 0, or 2 glands in this order).

*Petiole.*—Medium in thickness, and glandular near point of leaf attachment with the number of glands per petiole commonly ranging from 1 to 4 (most commonly 2). During the late summer and fall the coloration may change from green to Red-Purple Group 59A when exposed to the sun. When 26 representative leaves were measured during September, 1992, the average length of the petiole was approximately 0.9 cm.

Flowers:

*Size.*—Medium to small, and non-showy.

*Color.*—Pink to deep-rose pink, initially Red Group 55A, and changing to Red Group 56A at anthesis.

*Bloom time.*—Late season, with the N.J. 260 peach cultivar.

Fruit:

*Maturity when described.*—Eating ripe on Sep. 15, 1992, 15 days after harvest from the original limb mutation grown near Fairfield, Ill.

*Size.*—Medium to large, variable, and slightly smaller than the N.J. 260 cultivar on average. The axial diameter commonly measures approximately $2\frac{3}{8}$ to $2\frac{3}{4}$ inches. The transverse diameter in the suture plane commonly measures approximately $2\frac{5}{8}$ to 3 inches. The measurement at a right angle to the suture plane commonly is $2\frac{1}{2}$ to $2\frac{7}{8}$ inches.

*Shape.*—Commonly uniform, globose, symmetrical to occasionally slightly unsymmetrical. In the suture plane the ratio of the axial to transverse diameters commonly averages approximately 0.92:1. In the plane perpendicular to the suture plane the ratio of the axial to transverse diameters commonly averages approximately 0.95:1.

*Suture.*—Distinct, shallow, and extends from the base to slightly beyond the apex.

*Ventral surface.*—Rounded, slightly ridged on either side, lips unequal, and the most pronounced lip commonly varies from fruit to fruit on the right to left side.

*Stem cavity.*—Rounded, abrupt, and very slightly elongated in the suture plane. The depth commonly ranges from 5 to 12 mm. (e.g., 9 mm). The breadth in the suture plane commonly ranges from 18 to 25 mm. (e.g., 22 mm.). The width perpendicular to the suture plane commonly ranges from 15 to 20 mm. (e.g., 18 mm.).

*Base.*—Slightly truncate to rounded, and retuse.

*Apex.*—Slightly depressed, short, and emarginate.

*Pistil point.*—Apical and acuminate.

*Stem.*—Short in length, glabrous, and medium in thickness.

*Skin.*—Glabrous, thin to medium in thickness, tender to moderate in texture, and moderately tenacious to the flesh. Splashed, slightly striped, and blushed with red, commonly averaging 70 to 75 percent of the surface with Red Group 46A lightening to Red Group 47A, over a deep yellow ground color, Yellow-Orange Group 19A. Also, the pattern of the over color commonly is more mottled and splashed than that of the N.J. 260 peach cultivar.

Flesh:

*Color*—Yellow, Yellow-Orange Group 22C, and speckled to mottled with red adjacent the stone.

*Surface of pit cavity.*—Scattered yellow with pink to red coloration and pink fibers.

*Texture.*—Melting and buttery when eating ripe, and slightly more dense and rubbery than that of the N.J. 260 peach cultivar when under-ripe or shipping-ripe.

*Fibers.*—Few, fine, and tender.

*Ripening ability.*—Fairly evenly.

*Flavor.*—Subacid to mildly acid, delicate and mild.

*Aroma.*—Pronounced.

*Eating quality.*—Good.

Stone:

*Attachment.*—Free.

*Fibers.*—Moderate in length with some tendency to be attached to the pits.

*Size.*—Medium-large. Equal in size to that of N.J. 260 peach cultivar in 1991, and larger on average than that of the N.J. 260 peach cultivar during 1992 and 1993. Commonly measures 37 to 41 mm. in length, and 29 to 32 mm. in width.

*Form.*—Obovoid, and fully cuneate towards the apex.

*Base.*—Oval to slightly truncate.

*Apex.*—Acuminate and slightly recurved towards the ventral edge (opposite of the suture).

*Sides.*—Mostly equal.

*Surface.*—Irregularly furrowed near the base, apex and dorsal edge, and pitted in the center. The ridges are ragged to rounded, and tend to be rounded in the center and ragged towards the edges.

Use: Fresh market, dessert.

Keeping quality: Good.

Resistance to Insects: Substantially similar to the N.J. 260 peach cultivar.

Resistance to diseases: The fruit may be more susceptible to diseases affecting the skin finish than that of the N.J. 260 peach cultivar due to the total lack of pubescence.

Shipping quality: Good.

I claim:

1. A new and distinct late-season nectarine cultivar, having the following combination of characteristics:

(a) forms fruit of good flavor and texture that is substantially similar to that of the N.J. 260 cultivar with the exception that it is lacking in pubescence, (b) forms fruit that commonly matures approximately 3 to 5 days earlier than that of the N.J. 260 cultivar, (c) forms fruit that commonly is slightly smaller than that of the N.J. 260 cultivar, and (d) exhibits an overall growth habit that is substantially similar to that of the N.J. 260 cultivar;

substantially as herein shown and described.

* * * * *